Jan. 15, 1974 A. W. FISCHER Plant Pat. 3,441
AFRICAN VIOLET PLANT
Filed Jan. 24, 1972
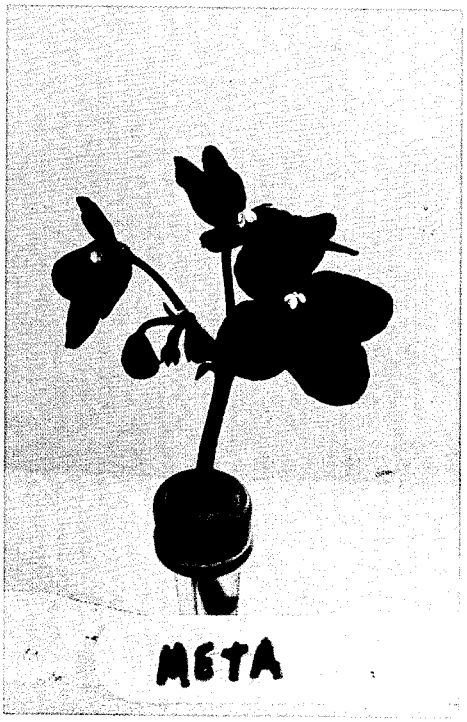
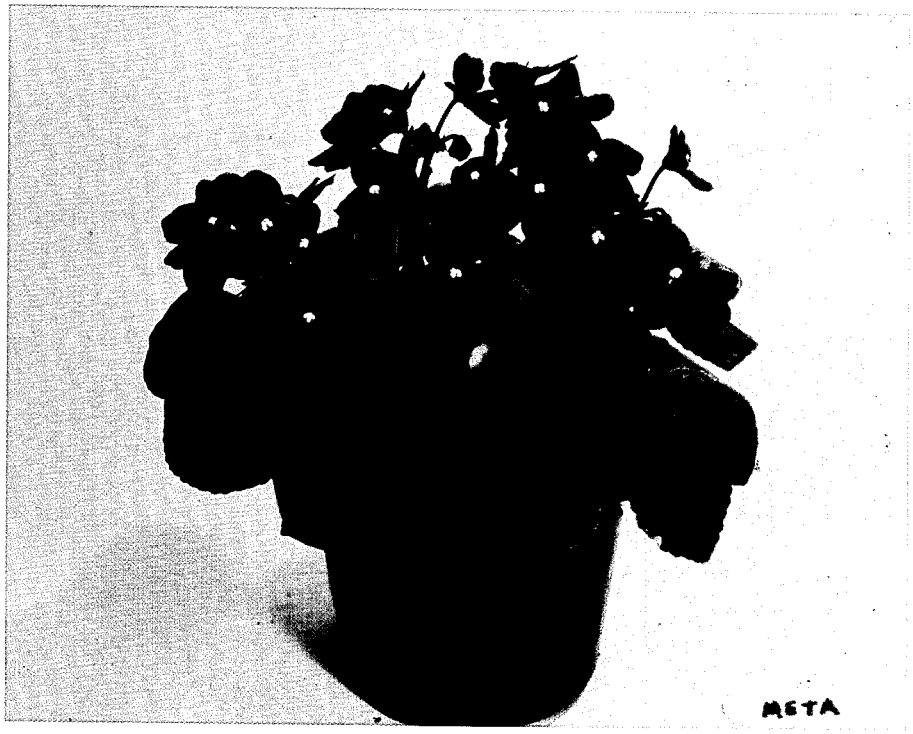

United States Patent Office

Plant Pat. 3,441
Patented Jan. 15, 1974

3,441
AFRICAN VIOLET PLANT

Arnold W. Fischer, Isernhagen, Germany, assignor to Geo. J. Ball, West Chicago, Ill.

Filed Jan. 24, 1972, Ser. No. 220,509
Int. Cl. A01h 5/00
U.S. Cl. Plt.—69 1 Claim

ABSTRACT OF THE DISCLOSURE

A new variety of African violet plant distinguished by the deep violet color of its blossoms, which bloom recurrently the year around, its sturdy and relatively long upright flower stalks which display the flowers high above the foliage, and its abundant production of plantlets during cut leaf propagation.

BACKGROUND OF THE INVENTION

This new variety of African violet plant originated as a seedling in my greenhouse of Isernhagen, Germany, where I have been carrying on the breeding and culture of African violet plants with the object of developing improved varieties of these plants for the house plant market. This new plant is much like another of my African violet varieties identified by the name "Gerda" and was selected for asexual reproduction and test because this plant appeared to have an earlier flowering habit and a more upright flower stalk than "Gerda," because the blossoms are larger and almost flat compared to those of "Gerda," and because the flowers are displayed at a greater height above the foliage. Asexual propagation of this plant was done under my direction, by means of leaf cuttings, at Isernhagen, Germany, and such propagation through several generations has demonstrated that this plant retains all of the distinctive characteristics of the original plant. Commercial propagation of this plant is now being carried on at West Chicago, Ill., U.S.A., by means of leaf cuttings and division of shoots.

DESCRIPTION OF THE DRAWING

This new variety of African violet plant is illustrated by the accompanying drawing which shows the form and color characteristics of the plant and its blooms, the color rendition being as nearly true as is reasonably possible to obtain by conventional photographic procedures. The upper view shows details of the flowers and the manner in which they are borne on the branches extending from the flower stalk; and the lower view shows the entire plant in full bloom. The color patches A and B show the true colors of the top and under sides, respectively, of the flower petals.

DESCRIPTION OF THE NEW PLANT

The following is a detailed description of my new variety of African violet plant with color descriptions according to the Horicultural Colour Chart published by the British Colour Council in collaboration with the Royal Horicultural Society of London, England.

*The plant*

Origin: Seedling
Parentage:
- *Seed parent*—*A Saintpaulia ionantha* of unknown origin
- *Pollen parent*—Blaues Mäerchen (unpatented)

Classification:
- *Botanic*—*Saintpaulia ionantha*
- *Commercial*—African violet Form: Compact potted plant (rosette arrangement)

Height: About 3 inches from the base at soil level to the top of the flowers
Growth: Condensed, upright and fairly strong
Foliage: Plentiful but not very compact
- *Size of leaf*: 2 inches wide at midpoint and 2 inches long in the mature leaf
- *Shape of leaf*: Generally oblong-ovate with crenate margins
- *Texture.*—Leathery and tough with both sides of the leaf very tomentose
- *Veins.*—Pinnate—veins are very pronounced on under side of leaf, usually 4 very obvious veins on each side of the leaf
- *Color.*—Upper side—Leek Green 181. Under side—Veronese Green 660/2
- *Petioles.*—Up to 2¼ inches long depending upon age of leaf

*The bud*

Form: Pear-shaped
Size: Small—¼ inch in diameter and ¼ inch in depth just before opening
Opening: Very slowly—5 weeks from visible bud until flower opens
Color: When petals unfurl—Victoria Violet 738
Sepals: Hooded over bud for a very short time
- *Form.*—Sepals are 5-branched, stand up and are spear-shaped
- *Color.*—Inside—Fern Green 0862. Outside—Willow Green 000862

Calyx: Splits to star shape
- *Aspect.*—Smooth on inside, very tomentose on the outside Peduncle:
- *Length.*—1¼ to 2 inches long from base to branching. Branch length—⅝ inch to 1 inch long
- *Strength.*—Flexible and fairly erect
- *Aspect.*—Very tomentose
- *Color.*—Maroon 1030

*The flower*

Blooming habit: Recurrent the year around with tendency to earlier blooming than "Gerda"
Size of flower: Average flower is of medium size but many are larger with diameters 15/16 inch to 1½ inches. Generally flat in form with 2 smaller petals held upwardly at a 10 to 25 degree angle forming a flower depth of about ¼ inch.
Borne: In cluster on each primary peduncle
Petalage: Number of petals—5, 3 being noticeably larger than the remaining 2
- *Arrangement.*—Sympetalous (fused)
- *Form.*—Rotate, with bilateral symmetry and very smooth edges
- *Color.*—Face side—Victoria Violet 738. Reverse side—Victoria Violet 738/3
- *Texture.*—Soft
- *Appearance.*—Velvety, tomentose on reverse or under side Peduncle: 1¼ to 2 inches long from base to branching, branches ⅝ inch to 1 inch long
- *Strength.*—Sturdy and upright
- *Color.*—Maroon 1030

Discoloration after full bloom: Color becomes darker
Effect of temperature conditions: Hot environment suppresses flowering. Plant thrives in mild temperature and 80% to 90% relative humidity.
Fragrance: None
Lasting quality: 10 to 14 days for fully opened flower
Persistence: Blossoms hang on and dry

*Reproductive organs*

Stamens:

*Anthers.*—Arrangement basifixed, 2 in number, each ⅛ inch long and made up of 2 anther cells fused together

*Filaments.*—Single filament 3/16 inch to ¼ inch long. Color: Victoria Violet 738/2 surrounding Sap Green 62/2

*Pollen.*—Color: White

Pistils: One in number, 7/16 inch long. The pistil emerges from beneath the anthers on the side of the two small petals and hangs over the three large petals.

Stigmas: Aconite Violet 937/2 in color

Style: 3/16 inch long and Aconite Violet 937/2 in color

Ovaries: Tomentose and Pod Green 061 in color. After opening, the base of the ovary is yellow.

This variety of African violet plant is very much like the variety "Gerda" particularly with respect to its color. Specific distinctions of this variety over the variety "Gerda" are to be found in that the flowers of this variety are flatter than those of "Gerda," the foliage is less abundant and the leaves are more pointed than those of "Gerda." The blossoms of this variety are larger than those of "Gerda" and appear on stalks and branches that are longer than those of "Gerda" so that the mass of blooms appears to be taller and more dense in form than that of "Gerda." Other distinctions will be found in that the veins of the leaves of this variety do not connect at the outer edges of the leaves as they do in "Gerda" and this variety has the distinct advantage of producing plantlets abundantly in the course of cut leaf propagation.

I claim:

1. A new variety of African violet plant, substantially as herein shown and described, characterized by the relatively large flowers which are substantially flat when fully opened, the larger and more pointed leaves, the veins of which do not connect at the edges of the leaves, the longer flower stalks and branches which display the blossoms well above the foliage, and the capability of producing more abundant plantlets from each cut leaf in the process of cut leaf propagation.

No references cited.

ROBERT E. BAGWILL, Primary Examiner